United States Patent [19]

Hain et al.

[11] Patent Number: 4,482,322
[45] Date of Patent: Nov. 13, 1984

[54] DEVICE FOR SURFACE TREATMENT OF TEETH

[75] Inventors: Josef Hain, Laudenbach; Hermann Landgraf, Heppenheim, both of Fed. Rep. of Germany

[73] Assignee: Siemens Aktiengesellschaft, Berlin & Munich, Fed. Rep. of Germany

[21] Appl. No.: 478,095

[22] Filed: Mar. 23, 1983

[30] Foreign Application Priority Data

Apr. 1, 1982 [DE] Fed. Rep. of Germany ....... 3212207

[51] Int. Cl.³ .............................................. A61C 3/02
[52] U.S. Cl. ..................................... 433/88; 51/436; 51/438
[58] Field of Search .................... 433/88, 125, 216; 251/53; 51/426, 427, 428, 436, 437, 438, 439; 118/308; 222/630, 173

[56] References Cited

U.S. PATENT DOCUMENTS

| | | |
|---|---|---|
| 2,696,049 | 12/1954 | Black ...................................... 433/88 |
| 2,814,877 | 12/1957 | Tilden .................................... 433/88 |
| 3,141,264 | 7/1964 | Moore ................................... 51/438 |
| 3,199,844 | 8/1965 | Moore et al. ......................... 51/438 |
| 3,631,631 | 1/1972 | Greenstein ........................... 51/427 |
| 3,798,841 | 3/1974 | Eppler .................................. 51/436 |
| 4,067,150 | 1/1978 | Merrigan .............................. 51/436 |
| 4,075,789 | 2/1978 | Dremann .............................. 51/436 |
| 4,174,571 | 11/1979 | Gallant ................................ 433/88 |

Primary Examiner—John J. Wilson
Attorney, Agent, or Firm—Hill, Van Santen, Steadman & Simpson

[57] ABSTRACT

A device for surface treatment of teeth characterized by a vortex chamber divided by a diaphragm into an upper and lower portion, a reservoir discharging through an orifice which is positioned in the first portion to be closed by the diaphragm while in a first position, a pressurized gas line discharging into the first portion and extending from the first portion to a nozzle of the device so that an abradant discharged through the orifice into the first portion is mixed with the gas for discharge from the nozzle of the hand piece. The second portion of the vortex chamber includes a spring biasing the diaphragm toward the first position and a control line which receives pressurized gas from a branching line and has a regulating valve for venting the gas pressure in the second chamber to enable the diaphragm to move to the second position to enable flow of the abradant into the first portion. The device also includes a vibrating arrangement for vibrating the reservoir and the reservoir is pressurized by a pressure compensation line extending from the discharge side of the gas line to the reservoir.

16 Claims, 4 Drawing Figures

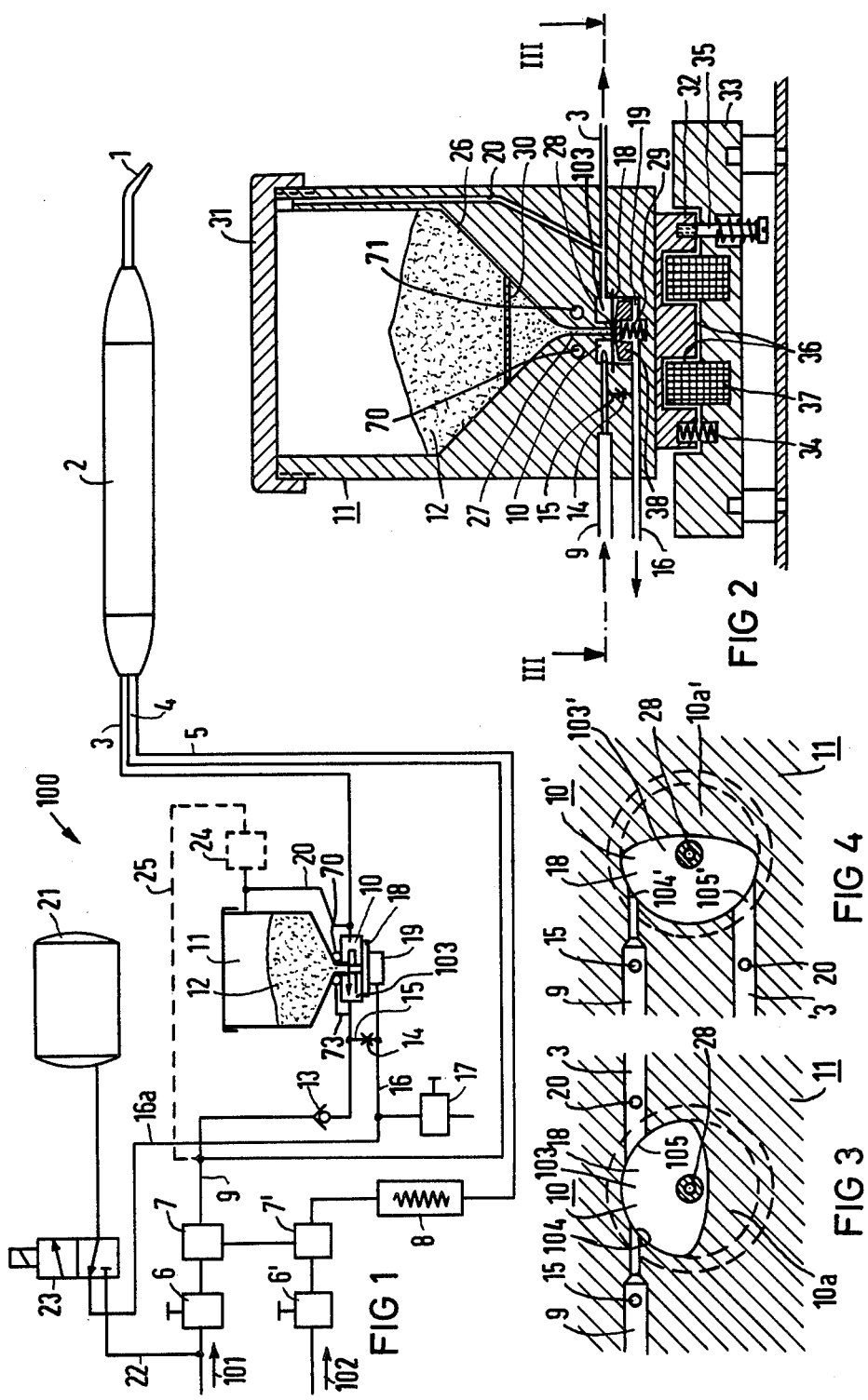

DEVICE FOR SURFACE TREATMENT OF TEETH

BACKGROUND OF THE INVENTION

The present invention is directed to a device for the surface treatment of teeth particularly for removing dental deposits, which device has means for creating a gas stream with an abradant, said means including a gas line extending from a compressed gas source to a nozzle, a reservoir for the abradant having a discharge orifice in communication with the gas line, a pressurization means for applying a pressure to the interior of the reservoir, including a pressure compensation line extending between the gas line to the reservoir and vibrating means coupled to the reservoir to vibrate the reservoir during operation of the device.

Devices which utilize a stream of gas or air mixed with an abrasive compound that was received in a reservoir and mixed into the air stream are known and examples are disclosed in U.S. Pat. Nos. 2,696,049 and 2,814,877. The aim of these devices is to introduce an abrasive which is in fine grained form from a reservoir into a gas or compressed air line which is leading to a discharge nozzle in the desired dosage. However, problems will occur with the abrasive particles becoming stuck together to create plugging of the lines and the valves.

SUMMARY OF THE INVENTION

The present invention is directed to providing a device which overcomes the problems of the abrasive material becoming stuck together to create stoppages in the lines and valves and which device produces a continuous flow of the desired dosage for mixture of the fine grained abrasive and compressed air or gas. To accomplish these goals, the present invention is directed to an improvement in a device having means for creating a gas stream containing an abradant, said means including a gas line extending from a compressed gas source to a nozzle, a reservoir for the abradant having a discharge orifice in communication with the gas line, a pressurization means for applying a pressure to the interior of the reservoir including a pressure compensation line extending from the gas line to the reservoir and vibrating means coupled to the reservoir to vibrate the reservoir during operation of the device. The improvements comprise a vortex chamber, a diaphragm extending across the vortex chamber to form a first and second portion and being movable between a first and second position, said gas line having an incoming portion discharging through an incoming port into the first portion of the vortex chamber and having an outgoing port in the first portion of the chamber which extends to an outgoing line that goes to the nozzle, said discharge orifice being positioned in the first portion of the chamber at a position to be closed by the diaphragm when it is in the first position, said second portion of the vortex chamber having a spring means for biasing the diaphragm to the first position, an air control line being in communication with the second portion, said air control line having a venting means including a regulatory valve for connecting the control line to the atmosphere and a branch line with a restriction connecting the air control line to the incoming portion of the gas line so that with a flow of gas through the gas line and the control line being vented to the atmosphere, the diaphragm moves away from the first position to allow abradants to pass through the discharge orifice into the first portion of the vortex chamber for mixing with the gas passing therethrough.

Preferably, the first portion of the vortex chamber has at least a portion of its wall which is a cylindrical shape and both the incoming and outgoing ports are tangentially arranged to this portion so that the gas enters the first portion tangentially, swirls therearound and is removed tangentially. Preferably, the discharge orifice is disposed eccentrically relative to the first portion of the chamber so that miscontrol of the diaphragm due to compressed air rotating in the vortex chamber can be avoided.

The vibrating means may be created by a mechanical vibrating means utilizing compressed air to drive a ball in an annular path around a passage connecting the reservoir to the discharge opening. Another vibrating means includes mounting the reservoir on resilient elements leaving an air gap, providing an electromagnet on a base plate and intermittently energizing the electromagnet to create oscillation of the resiliently mounted reservoir. It may be desirable to place the diaphragm into oscillation by providing a pressure plate which is urged by the spring means against the diaphragm. If the pressure plate is effected by the magnetic field created by the electromagnet, then oscillating attraction of the plate imposes oscillation onto the diaphragm.

BRIEF DESCRIPTION OF THE DRAWINGS

FIG. 1 is a pneumatic diagram of the device of the present invention;

FIG. 2 is a cross-sectional view of a reservoir for the abradant of the device for the present invention;

FIG. 3 is a cross-sectional view taken along the lines III—III of FIG. 2; and

FIG. 4 is a cross-sectional view similar to FIG. 3 of an embodiment of the vortex chamber of the present invention.

DESCRIPTION OF THE PREFERRED EMBODIMENTS

The principles of the present invention are particularly useful in the device indicated at 100 and diagrammatically illustrated in FIG. 1. The device 100 as illustrated in FIG. 1 is preferably employed for tooth cleaning, particularly for removing plaque. As is already known in the prior art, a gas stream mixed with a fine grained abrasive or abradant, for example, sodium hydrogen carbonate (Na $HCO_3$) is discharged in such a device having nozzle 1 of a hand piece 2. Air is usually employed as the gas carrier. The abradant/gas mixture is usually also mixed with water before it strikes the surface to be cleaned or the air abradant mixture is directed at the object as water is also directed at the object. Accordingly, to supply the hand piece 2 with a mixture of the abradant and carrier gas or air, an abradant mixture conveying line 3 is provided. If need be for better acceleration of this mixture, additional abradant-free compressed air is supplied via a separate line 4 and water is supplied by another separate line 5. The three agents are conducted separately in separate lines through the hand piece and are mixed with one another either as they are discharged from the nozzle separately or just prior to being discharged from the nozzle. An example of a structure of a nozzle which will expediently provide these features is disclosed and described in copending U.S. patent application Ser. No. 408,124, filed Aug. 13, 1982, which application was based on German patent application No. P 31 32 291.3 and whose specification and disclosure is incorporated by reference thereto.

Device 100 receives a compressed gas such as compressed air from a source as indicated by an arrow 101 which passes through a pressure-reducing valve 6 that reduces it to the desired pressure and then through a solenoid control valve 7. In a similar manner, water from a source flows in a direction indicated by arrow 102, passes through a reducing valve 6' and a solenoid valve 7'. The water then passes through a heater 8 which will heat it to approximately body temperature so that the water sprayed through the nozzle 1 will be at approximately body temperature. The compressed air, after it passes through the solenoid valve 7, is in a compressed air supply line which has a check valve or one-way valve 13 and extends to a vortex chamber 10. The vortex chamber 10 is best illustrated in FIG. 2 and has a diaphragm 18 extending thereacross to subdivide the chamber 10 into a first upper portion 103 and a lower portion 19. As best illustrated in FIG. 3, the line 9 forms an incoming portion which has a port 104 and discharges into the first portion 103. From the first portion 103, the air or gas is discharged through an outgoing port 105 into an outgoing line 3 that extends to the nozzle 1 of the hand piece 2.

Above the vortex chamber 10, the device 100 includes a reservoir 11 which contains a supply of abradant 12 which is illustrated as being in bulk or powdery form. This abradant 12 of the reservoir 11 is discharged in a metered amount into the first portion 103 of the vortex chamber 10. To control this discharge, a control line 16 extends from the second portion 19 to a venting means which is illustrated as a regulating valve 17. The control line 16 is connected by a branch line 15 which contains a restriction 14 to the incoming portion of the gas supply line 9. It should be noted that the outgoing portion of the gas line 3 has branching therefrom a pressure compensation line 20 that discharges into the reservoir 11 adjacent an upper area. The device 100 also includes an accumulator 21 which will be filled by compressed air from the source by a line 22 which extends to a reversing valve 23. In one switch position, the line 22 is connected to the accumulator 21 for charging. In the position illustrated, the accumulator 21 is connected by the valve 23 to a line section 16a that extends to the control line 16. The device 100 also may include a high speed depressurizing valve 24 which is located in the upper reservoir part such as in the reservoir cover. The valve 24 may be connected to a compressed air supply line 9 or, respectively, the line 4 by a line 25 which is illustrated in broken lines.

The above description is basically directed to a diagrammatic presentation. The reservoir 11 preferably has a structure illustrated in FIG. 2 and exhibits slanting or preferably a funnel-shaped bottom wall 26 which merges into a down pipe or line 27 which has a discharge orifice 28 which discharges into the first portion 103 of the vortex chamber 10. When the device is in a rest condition, the diaphragm 18 is in a first position which closes the discharge opening 28 and is held there by a compression spring 29 so that no abradant can proceed from the reservoir 11 into the first portion 103 of the vortex chamber. This is particularly desirable for portable devices. In order to obtain a certain size classification of the granules of the abradant 12 which is placed in the reservoir 11, a sieve 30 is provided. Also, in the device illustrated, the pressure compensation line 20 is integral with the housing of the reservoir 11 and discharges into the inside of the container tangentially below a cover 31 which is threaded onto the upper end of the housing to form an air-tight seal. The tangential entry of the pressurized compensation line 20 into the reservoir space has the advantage that when the device is turned on, air flowing through the line 20 into the reservoir space is swirled there in a controlled manner. As best illustrated in FIG. 3, the incoming port 104 and the outgoing port 105 for the portions 9 and 3, respectively, are tangentially arranged in the upper or first portion 103 of the vortex chamber 10. Also, they are disposed opposite one another so that the direction of incoming flow and outgoing flow is the same. Preferably, the vortex chamber 10 in the upper portion 103 only takes up a portion or part of the circular surface of the diaphragm 18. A fixed projection 10a takes up the other part. The discharge opening 28 is eccentrically positioned relative to the upper portion 103 of the vortex chamber and the presence of the projection 10a provides the advantage that the diaphragm is not unintentionally displaced due to air swirling in the chamber 103.

In another desirable embodiment of the construction of the vortex chamber the inlet port 104' of the incoming portion 9 and an outlet port 105' of an outgoing portion 3' are arranged to be tangential to the upper portion 103' of the vortex chamber 10', however, as illustrated in FIG. 4, they do not proceed in the same direction but are disposed in opposite directions. In addition, a projection 10a' is offset approximately 90° from the position of the projection 10a in FIG. 3. As a result, a swirling is particularly intensive with the air as it enters the portion 103' and prior to its discharge through the outgoing port 105'.

In order to provide means for vibrating the reservoir 11 to aid in discharge of the abradant 12, the reservoir 11 has an essentially planar base plate 32 which is received in a recess of a pedestal base 33 so that it can move therein. As illustrated, this is accomplished by resiliently mounting the base plate 32 so that it will float in the recess and provide an air gap 36. To accomplish this, the mounting utilizes three compression springs 34 and a screw 35 which are each circumferentially spaced around the base plate 32. The screw 35 is resiliently joined to the base or pedestal 33. The pedestal 33 includes an electromagnetic coil 37 which is connected to an AC current of preferably 24 volts so that an alternating magnetic field is created to cause the base plate 32 to vibrate and thus vibrate or shake the reservoir 11.

Instead of utilizing electromagnetic vibrating means, a mechanical vibrating means can also be utilized. The mechanical vibrating means can take the form of a weight being driven in a circular path by compressed air to create an eccentric shaking motion. For example, it can be an annular chamber 70 (see FIG. 2) which is disposed around the passage 27 and receives a ball 71. To drive the ball 71, compressed air can be supplied from the air line 9 via an air line 73 illustrated in FIG. 1.

As illustrated in FIG. 2, the spring 29 preferably acts through a pressure plate 38 which has a curved upper surface which may be considered a mushroom cap shape. In comparison to the diaphragm, the mushroom-shaped pressure plate 38 is relatively heavy and preferably is manufactured of metal. If an electromagnetic vibrating means is utilized, and if the pressure plate is of a ferromagnetic material, then the plate 38 which is supported on the spring 29 will be placed in a periodic oscillation during operation of the electromagnetic vibrating means. This will result in the diaphragm 18 being placed in a periodic oscillation during operation of the device to create a uniform feed of the abradant. Particularly, blockage of the feed or discharge opening 28 due to a larger grain can be avoided even when different grain sizes of the abradant are being utilized. It should be noted that the abradant grain size can lie between 3 and 150 μm.

The operation of the device is followed. In an off or idle condition, the gas line 9 receives no pressure and thus the diaphragm 18 will be in the first position and close the orifice 28 of the reservoir. This is due to the spring 29 acting on the mushroom cap-shaped pressure plate 28 to hold it tightly against the diaphragm.

On placing the device in operation, the two solenoid valves 7 are actuated in a known manner by means of a hand or foot switch and air and water streams are thus released. The compressed air then flows over the feed line 9 tangentially into the upper portion 103 of the vortex chamber 10 and also flows tangentially out of the ports 105 or 105' and the line 3 or 3' which extends to the nozzle 1. After the device has been turned on, the membrane 18 will remain closed until the pressure has built up uniformly in the system. Thus, no abradant can proceed into the upper portion of the vortex chamber and into the line connected thereto given an inadvertent, short engagement or energizing of the device. The space in the second portion 19 which is below the diaphragm 18 is then deaerated due to operation of the regulating valve 17 of the control line 16. It is noted that the connecting line 15 is connected to both chamber 19 as well as the control line 16 which leads to the regulating valve 17 (FIG. 1). By opening the regulating valve 17, the diaphragm is moved from its first position blocking flow from the orifice 28 toward a second position. The amount of movement of the diaphragm toward the second position will depend on the amount of opening of the regulating valve and thus the amount of the abradant 12 that can trickle into the upper portion 103 of the vortex chamber 10 can be controlled to a specific amount. If the pressure plate 38 is ferromagnetic and if an electromagnetic vibrating means is utilized, this will cause the diaphragm 18 to periodically oscillate in whatever position it assumes and as mentioned hereinabove, this oscillation will prevent blockage of the orifice 28.

As a result of the tangentially entering and discharging compressed air, an extremely favorable swirling of the abradant trickling into the first portion 103 is guaranteed. The compensation line 20 will insure a uniform aeration or a respective deaeration of the inside of the reservoir 11. A slow opening and a setting of the opening gap at the orifice 28 as well as low air consumption are achieved with the restriction 14 which is disposed in the branching line 15.

The accumulator 21 (FIG. 1) is provided in order to avoid any afterblow of the abradant after the device has been shut down. Thus, during operation of the device, the reversing valve 23 is situated in a position in which it connects the line 22 to the accumulator 21 so that the accumulator is thus filled with compressed air. After the device has been shut off or shut down by means of closing the solenoid valves 7 and 7', the reversing valve 23 is transferred into the illustrated position and the compressed air which has been received in the accumulator 21 is connected through the line 16a and the control line 16 to the second portion 19 so that the diaphragm 18 is further urged by the spring 28 and the compressed air in the lower portion 19 to the first position to seal or close the orifice 28.

Another manner or way of avoiding afterblow or for reducing it consist in depressurizing the reservoir 11 through the valve 24 and the line 25 which discharges into the compressed air line 4. Thus, when the device is shut down by actuation of the solenoid 7 and 7', the valve 24 opens to remove the pressure in the reservoir 11.

As already mentioned, the orifice 28 of the downpipe or conduit 27 is not centrally but rather eccentrically disposed relative to the first portion of the vortex chamber 10. This arrangement gives a particularly functionally reliable control of the feed of the abradant. A potential suction of the diaphragm 18 due to air swirling in the upper portion 103 of the chamber 10 is thereby avoided.

While the illustrated embodiment of the reservoir 11 has a bottom wall 26 which has a conical shape to form a funnel-shaped floor or bottom terminating in the conduit or downpipe 27, the presence of the vibrating means means that other structural forms for the reservoir 11 can be utilized. Thus, a box-shaped structure having one or more obliquely disposed bottom walls which merge into a downpipe or respectively in an orifice such as 28 can be provided. A structure without the downpipe so that the abradant trickles directly from the container into the first portion of the vortex chamber 10 through the opening 28 is also possible.

Although various minor modifications may be suggested by those varied in the art, it should be understood that we wish to embody within the scope of the patent granted hereon, all such modifications as reasonably and properly come within the scope of our contribution to the art.

We claim:

1. In a device for surface treatment of teeth having means for creating a gas stream containing an abradant, said means including a gas line extending from a compressed gas source to a nozzle, a reservoir for an abradant having a discharge orifice in communication with the gas line, pressurization means for applying a pressure to the interior of the reservoir including a pressure compensation line extending from the gas line to the reservoir and vibrating means coupled to the reservoir to vibrate the reservoir during operation of the device, the improvements comprising a vortex chamber, a diaphragm extending across the vortex chamber to form a first portion and a second portion with the first portion having at least an arcuate wall segment, said diaphragm being movable between a first position and a second position, said gas line having an incoming portion discharging at an incoming port into the first portion of the vortex chamber and an outgoing portion connected by an outgoing port to the first portion of the chamber and extending to the nozzle, said incoming port and portion and the outgoing portion and port being arranged to be tangential to said arcuate wall segment, said discharge orifice being positioned in said first portion of the vortex chamber at a position to be closed by the diaphragm in said first position, said second portion having spring means for biasing the diaphragm to the first position, and an air control line being in communication with the second portion, said air control line having venting means including a regulating valve for connecting the control line to the atmosphere and a branch line with a restriction interconnecting the air control line to the incoming portion of the gas line so that with a flow through the gas line and the control line being vented to the atmosphere, the diaphragm moves away from the first position to allow abradants to pass through the discharge orifice into the first portion of the vortex chamber for mixing with the gas passing therethrough.

2. In a device according to claim 1, wherein the flow in the incoming port and the outgoing port is in the same direction.

3. In a device according to claim 1, wherein the flow in the incoming and outgoing ports is in opposite directions.

4. In a device according to claim 1, wherein the discharge orifice is disposed eccentrically relative to the first portion of the vortex chamber.

5. In a device according to claim 4, which includes means for placing the diaphragm into a periodic oscillation while in an open position.

6. In a device according to claim 5, wherein the means to place the diaphragm in a periodic oscillation includes a pressure plate being coupled to the vibrating means and being disposed between the spring means and the diaphragm.

7. In a device according to claim 6, wherein the pressure plate has a form of a mushroom cap.

8. In a device according to claim 6, wherein the vibrating means is an electromagnetic vibrating means and the pressure plate is a ferromagnetic material.

9. In a device according to claim 6, wherein the vibrating means is a mechanical vibrating means and said pressure plate being a heavy metal plate.

10. In a device according to claim 1, wherein the reservoir has a funnel-shaped floor discharging into a downpipe which terminates in said discharge orifice.

11. In a device according to claim 1, wherein the vibrating means comprises a mechanical vibrating means operating with compressed gas, said compressed gas being taken from the incoming portion of the gas line.

12. In a device according to claim 11, wherein the reservoir has a slanting bottom wall with a downpipe extending therefrom and terminating in the discharge orifice, said mechanical vibrating means comprising an annular space surrounding the downpipe, a ball being placed in the annular space for rotation in response to compressed gas being applied thereto.

13. In a device according to claim 1, wherein the reservoir has a base plate, said vibrating means including a pedestal, means comprising resilient elements for mounting the base plate of the reservoir on the pedestal with an air gap, an electromagnet adjacent the pedestal and means for supplying an AC current to create an alternating field to oscillate the base plate and attached reservoir.

14. In a device according to claim 1, which includes an accumulator, valve means having one position connecting the accumulator to a source of compressed gas and a second position connecting the accumulator to the control line so that when the device is stopped, the accumulator discharges into the control line to pressurize the second portion of the vortex chamber to urge the diaphragm to the first position.

15. In a device according to claim 1, which includes valve means operated as the device is shut off to vent the gas pressure in the reservoir.

16. In a device according to claim 1, wherein the pressure compensation line discharges tangentially into the reservoir.

* * * * *